(12) United States Patent
Hornsby

(10) Patent No.: US 8,096,487 B2
(45) Date of Patent: Jan. 17, 2012

(54) FLUID DISPENSER

(75) Inventor: James Russell Hornsby, St. Louis, MO (US)

(73) Assignee: S.C. Johnson & Son, Inc., Racine, WI (US)

( * ) Notice: Subject to any disclaimer, the term of this patent is extended or adjusted under 35 U.S.C. 154(b) by 419 days.

(21) Appl. No.: 12/420,997

(22) Filed: Apr. 9, 2009

(65) Prior Publication Data

US 2009/0256004 A1  Oct. 15, 2009

Related U.S. Application Data

(60) Provisional application No. 61/043,921, filed on Apr. 10, 2008.

(51) Int. Cl.
 *B05B 3/00* (2006.01)
(52) U.S. Cl. ............... 239/263.1; 239/263.2; 239/263.3; 239/332; 239/333
(58) Field of Classification Search ....... 239/263.1–265, 239/331–334, 329, 330
See application file for complete search history.

(56) References Cited

U.S. PATENT DOCUMENTS

| | | | |
|---|---|---|---|
| 2,728,689 A * | 12/1955 | Ransburg | ..................... 427/483 |
| 3,132,350 A | 5/1964 | Carlson | |
| 3,230,550 A | 1/1966 | Carlson | |
| 4,183,105 A | 1/1980 | Womack | |
| 4,216,553 A | 8/1980 | Haberle | |
| 4,218,013 A | 8/1980 | Davison | |
| 4,383,341 A | 5/1983 | Altman | |
| 4,872,225 A | 10/1989 | Wagner | |
| 5,452,485 A | 9/1995 | Ross | |
| 6,162,371 A | 12/2000 | Rees et al. | |
| 6,328,543 B1 | 12/2001 | Benecke | |
| 6,463,600 B1 | 10/2002 | Conway et al. | |
| 6,471,974 B1 | 10/2002 | Rees et al. | |
| 6,712,079 B2 | 3/2004 | Bredo et al. | |
| 6,792,956 B2 | 9/2004 | Bredo et al. | |
| 6,820,821 B2 | 11/2004 | Linstedt et al. | |

(Continued)

FOREIGN PATENT DOCUMENTS

FR  2715308 A1  7/1995

(Continued)

OTHER PUBLICATIONS

PCT/US2009/002214 International Search Report and Written Opinion dated Jun. 25, 2009.

*Primary Examiner* — Christopher Kim

(57) ABSTRACT

An automated sprayer for spraying the walls of a shower enclosure with a liquid cleanser is disclosed. The sprayer includes a bottle suitable for containing the liquid, a housing, a pump located in the housing wherein the pump is in fluid communication with the bottle, a rotatable dome-shaped spray head extending away from an opening in a surface of the housing, a spray nozzle positioned such that an outlet of the spray nozzle is positioned within an opening in a side wall of the rotatable spray head wherein the spray nozzle is in fluid communication with an outlet of the pump, a motor located in the housing, and a transmission operably coupled to a shaft of the motor, the rotatable spray head, and the pump. The transmission transfers rotational motion of the shaft of the motor to drive the pump and cause rotation of the rotatable spray head such that the liquid is sprayed radially away from and around the housing thereby providing a circular spray pattern that contacts the walls of the shower enclosure.

18 Claims, 8 Drawing Sheets

| U.S. PATENT DOCUMENTS | | | |
|---|---|---|---|
| 6,830,056 B2 | 12/2004 | Bredo et al. | |
| 7,021,494 B2 | 4/2006 | Mazooji et al. | |
| 7,308,990 B2 | 12/2007 | Mazooji et al. | |
| 7,337,989 B1 | 3/2008 | Penner et al. | |
| 2008/0048050 A1 | 2/2008 | Mazooji et al. | |

| FOREIGN PATENT DOCUMENTS | | |
|---|---|---|
| JP | 10-328059 | 12/1998 |
| JP | 2000201844 | 7/2007 |
| WO | 2004012778 A2 | 2/2004 |
| WO | 2004094067 A2 | 11/2004 |

* cited by examiner

FLUID DISPENSER

CROSS-REFERENCES TO RELATED APPLICATIONS

This application claims priority based on U.S. Provisional Application No. 61/043,921 filed Apr. 10, 2008.

STATEMENT REGARDING FEDERALLY SPONSORED RESEARCH

Not Applicable.

BACKGROUND OF THE INVENTION

1. Field of the Invention

The invention relates to devices, systems and methods for dispensing, distributing or delivering a substance. More particularly, the invention relates to a device and method for dispensing a liquid (e.g., a cleaner, disinfectant, deodorizer, etc.). More particularly, the invention relates to dispensing a liquid in an enclosed area or defined perimeter, including in situations in which a human operator is present or not, and/or is not required or desired. In one embodiment, the invention is especially well suited for automatically cleaning shower/bathing enclosures of the type typically found in homes.

2. Description of the Related Art

The walls/doors of shower enclosures can become mildewed, coated with soap build up, hard water and/or mineral deposits, or become otherwise soiled, during typical use. Removing these deposits and stains has in the past required one to scrub the walls and doors by hand, particularly if significant amounts of time have passed between cleanings.

To assist in this task, cleaning chemicals have been sprayed, squirted, or otherwise applied on the surfaces to be cleaned. The walls are then scrubbed with a cloth, brush, or scrubbing pad, and then rinsed with water.

More recently some of these cleaners have been designed so that the amount of scrubbing can be reduced or even eliminated without compromising cleaning, particularly where the cleaners are sprayed on a daily basis. These cleaners are designed so as not to themselves leave spots or other visible stains, even if not rinsed off for hours or days after application.

"No scrub" cleaners are preferably applied after the shower has been used. This is accomplished by a consumer keeping a pump spray bottle of the cleanser in or near the shower enclosure, remembering to do the spraying (which may be problematic if the consumer has just woken up), and being willing (or able) to spend the time necessary to spray the enclosure.

An alternative no scrub approach is to provide an automated sprayer device for a shower. For example, U.S. Pat. Nos. 6,820,821, 7,021,494, 7,308,990, and 7,337,989 disclose automated cleansing sprayers that use an internal pump to spray cleaning fluid from a reservoir out from a rotating nozzle against enclosure walls. One presses an activation button, leaves the shower, and lets the device run through a spraying cycle. There is no need for scrubbing the enclosure walls, or rinsing off the cleaning liquid.

Notwithstanding this variety of automated sprayer devices, a need still exists for alternative automated sprayer devices that can be used to spray the walls of an enclosure with a liquid.

SUMMARY OF THE INVENTION

The present invention meets the foregoing need for an automated sprayer device. In one aspect, the invention provides an automated sprayer for spraying an enclosure with a liquid. The sprayer includes a bottle suitable for containing the liquid, a housing, a pump located in the housing wherein the pump is in fluid communication with the bottle, a rotatable dome-shaped spray head extending away from an opening in a surface of the housing, a spray nozzle positioned such that an outlet of the spray nozzle is positioned within an opening of the rotatable spray head wherein the spray nozzle is in fluid communication with an outlet of the pump, a motor located in the housing, and a transmission operably coupled to a shaft of the motor, the rotatable spray head, and the pump. The transmission transfers rotational motion of the shaft of the motor to drive the pump and cause rotation of the rotatable spray head such that the liquid is sprayed radially away from and around the housing.

In one form, the transmission is a gear box assembly. The pump can be operably coupled to a pump drive gear of the gear box assembly, and the pump drive gear can be operably coupled to a push rod that reciprocates a piston in a cylinder of the pump. The gear box assembly can be enclosed in a case, and the spray nozzle can include a tubular fluid inlet in fluid communication with the outlet of the pump, and the tubular fluid inlet can extend through an aperture in the case. The tubular fluid inlet can be mounted in a central opening of a spray nozzle drive gear of the gear box assembly.

In one version of the sprayer, the rotatable spray head extends axially above the opening in an upper surface of the housing. A hook can be included for mounting the sprayer in the enclosure, and the transmission can be located above the motor and the pump when the sprayer is mounted in the enclosure. The housing and the rotatable spray head can be located above the bottle when the sprayer is mounted in the enclosure.

The housing of the automated sprayer can include a bottle coupler having internal threads for engaging mating threads on a neck of the bottle. The bottle coupler can include a liquid passageway in fluid communication with an inlet of the pump and an air vent passageway in fluid communication with an interior of the housing. In one form, the air vent passageway is in fluid communication with a check valve. A lower end of the housing can include a bottle interface for engaging a neck of the bottle wherein the bottle interface includes at least one compartment for an energy source for the motor.

The automated sprayer can include a control circuit in electrical communication with a power source and the motor wherein the control circuit initiates a spray cycle of the sprayer upon movement of an actuator by providing power from the power source to the motor, and the control circuit automatically terminates the spray cycle by ceasing providing power from the power source to the motor. The control circuit can include a timer that delays providing power from the power source to the motor for a predetermined time after movement of the actuator.

In another aspect of the invention, there is provided an automated sprayer for spraying an enclosure with a liquid. The sprayer includes a bottle suitable for containing the liquid, a housing, a pump located in the housing wherein the pump is in fluid communication with the bottle, a rotatable dome-shaped spray head extending axially above an opening in an upper surface of the housing, a spray nozzle positioned such that an outlet of the spray nozzle is positioned within an opening of the rotatable spray head wherein the spray nozzle is in fluid communication with an outlet of the pump, a motor located in the housing, an energy source located in the housing wherein the energy source is in electrical communication with the motor, and a gear box assembly located in the housing. A first gear of the gear box assembly is operably coupled to a shaft of the motor, a second gear of the gear box assembly is operably coupled to the rotatable spray head, and a third gear of the gear box assembly is operably coupled to the pump. The gear box assembly transfers rotational motion of the shaft to drive the pump and to cause rotation of the rotatable spray head such that the liquid is sprayed radially away from and around the housing.

In one version of the automated sprayer, the gear box assembly is enclosed in a case, the spray nozzle includes a tubular fluid inlet in fluid communication with the outlet of the pump, and the tubular fluid inlet extends through an aperture in the case. The tubular fluid inlet can be mounted in a central opening of the second gear of the gear box assembly. The automated sprayer can include a hook for mounting the sprayer in the enclosure, and the gear box assembly can be located above the motor and the pump when the sprayer is mounted in the enclosure. The housing and the rotatable spray head can also be located above the bottle when the sprayer is mounted in the enclosure.

The advantages of the present invention will become apparent from the following description. In that description reference will be made to the accompanying drawings which form a part thereof, and in which there is shown by way of illustration example embodiments of the invention. The example embodiments do not limit the full scope of the invention.

BRIEF DESCRIPTION OF THE DRAWINGS

Like reference numerals will be used to refer to like parts from Figure to Figure in the following detailed description.

DETAILED DESCRIPTION OF THE INVENTION

Figure 1:
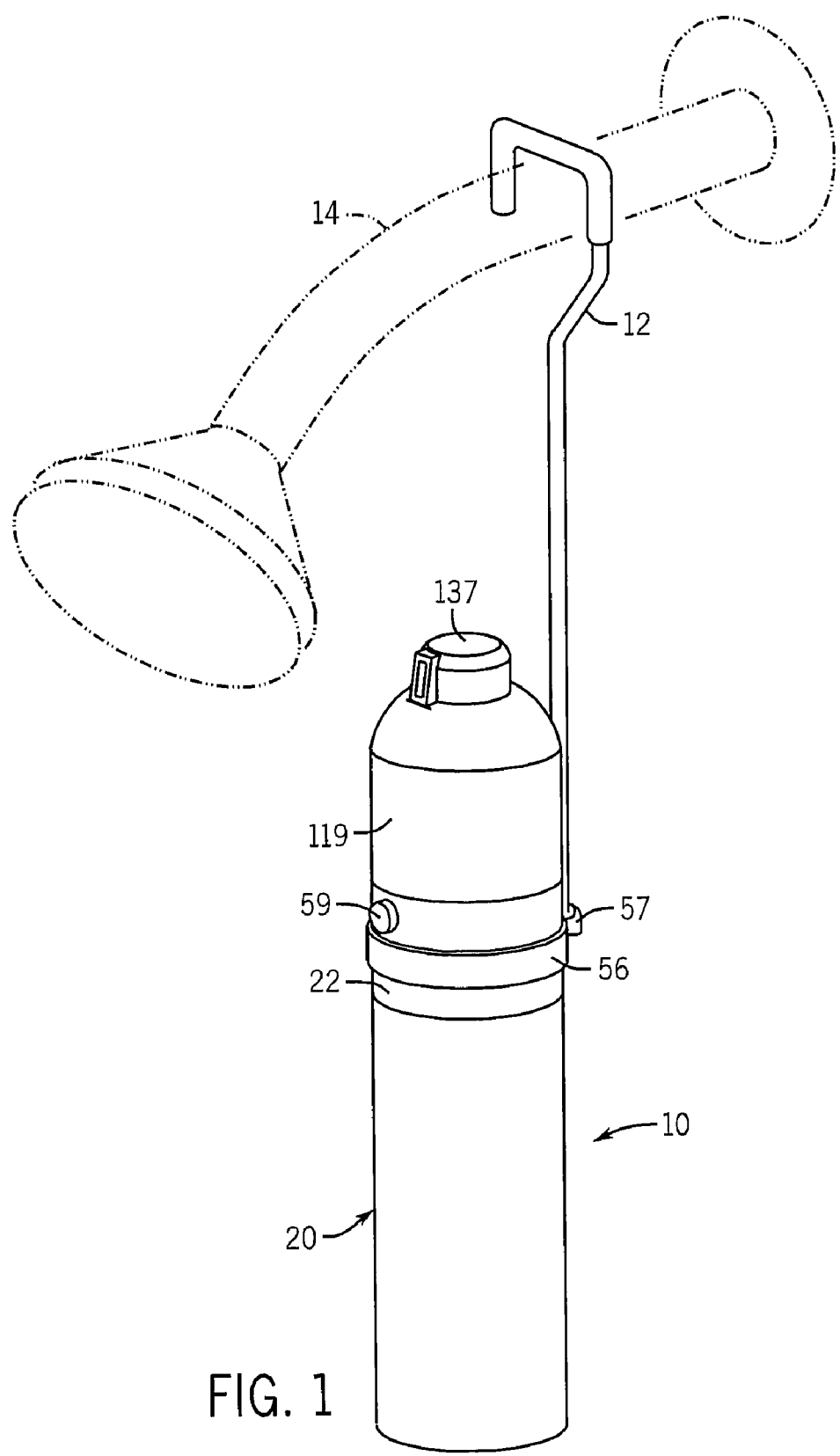
FIG. 1 is a perspective view of an automated sprayer in accordance with the invention suspended from a shower spout.

Looking at FIGS. 1-9 and 12, there is shown an example embodiment of an automated sprayer 10 according to the invention. The sprayer 10 includes a hook 12 for suspending the sprayer 10 from a shower spout 14 as shown in FIG. 1. The sprayer 10 is especially well suited for automatically spraying the walls of a shower/bathing enclosure with a liquid suitable for cleaning and/or freshening and/or disinfecting the walls without the need for rinsing the walls.

Figure 2:
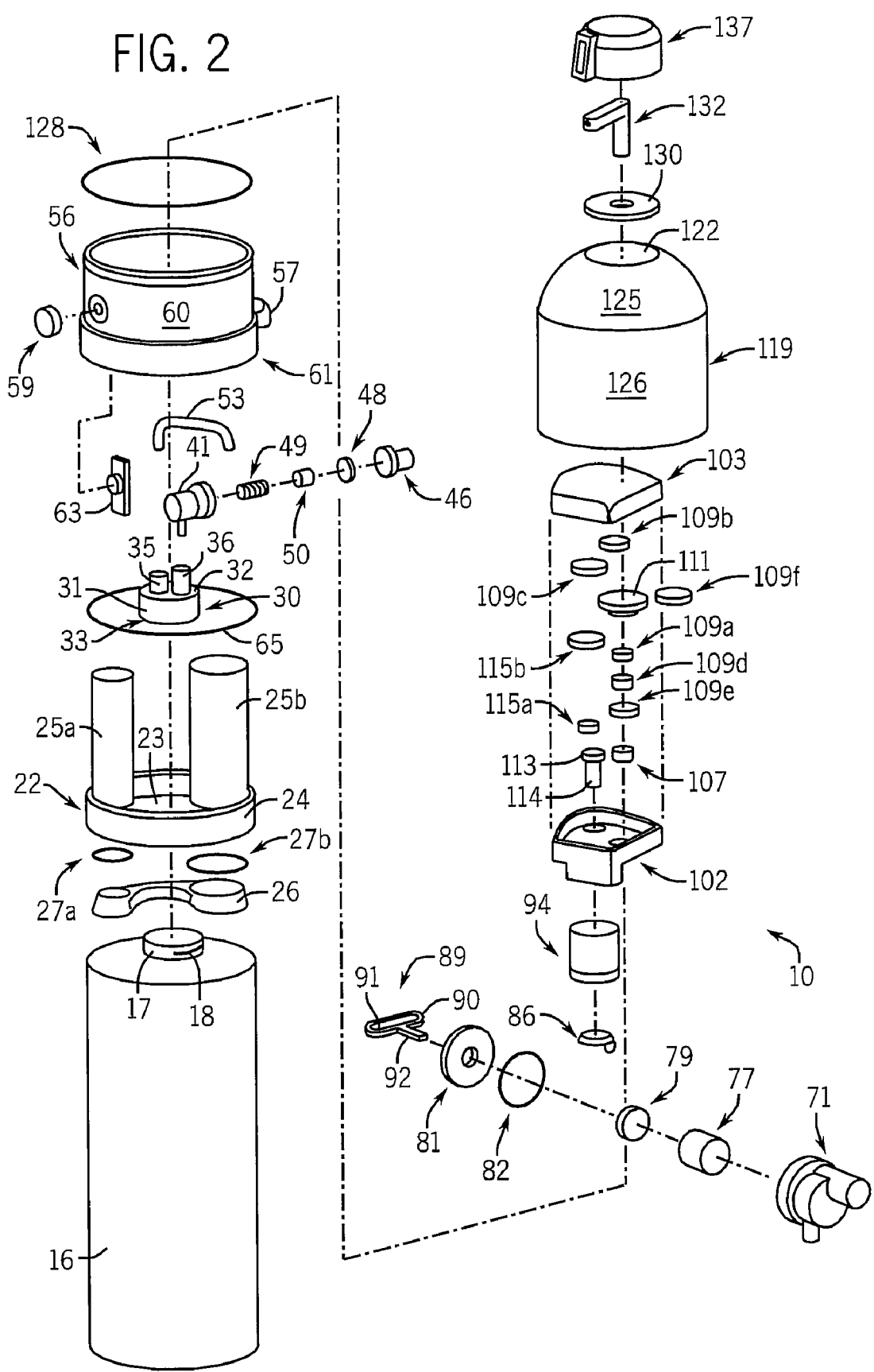
FIG. 2 is an exploded perspective view of the automated sprayer of FIG. 1.
Figures 3, 4:
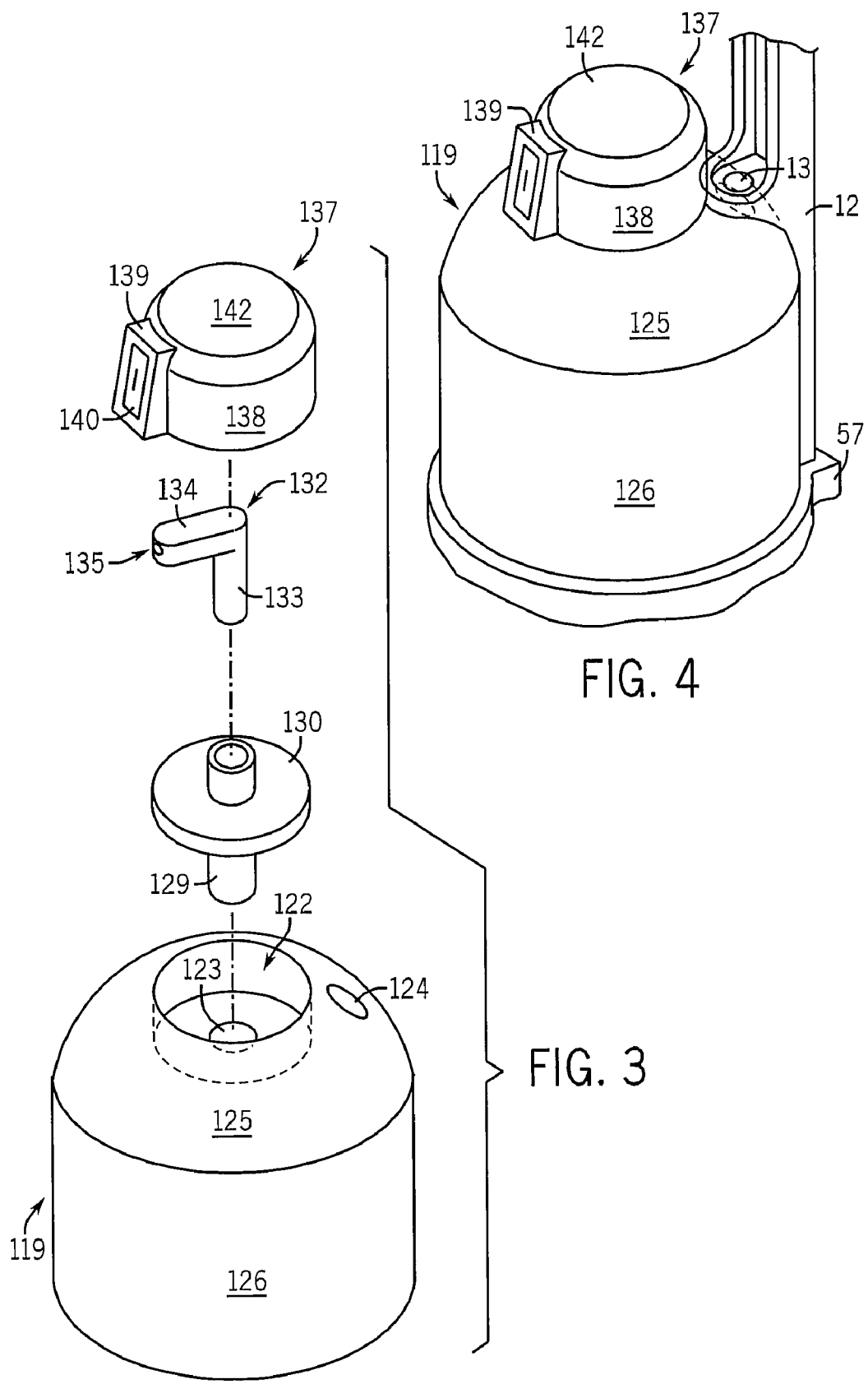
FIG. 3 is a partial exploded perspective view of the sprayer head and upper housing of the automated sprayer of FIG. 1.
FIG. 4 is a partial perspective view of the sprayer head and upper housing of the automated sprayer of FIG. 1.

Referring to FIG. 2, the sprayer 10 includes a bottle 16 having a hollow neck 17 with external threads 18. The bottle 16 is suitable for containing a liquid for cleaning and/or freshening and/or disinfecting a hard surface such as a wall of a shower/bathing enclosure. Example liquid formulations for use on a wall of a shower enclosure can be found in U.S. Pat. Nos. 6,471,974 and 6,162,371 which are incorporated herein by reference. The bottle 16 may be supplied with a closure (not shown) that is screwed onto the neck 17. The closure keeps the liquid contained in the bottle 16 before the bottle 16 is installed in the sprayer 10. The bottle 16 is typically formed from a suitable polymeric material such as polyethylene, polypropylene, or polyethylene terephthalate. The threads may be either the so-called "conventional" threads or the so-called "bayonet"-type threads.

Looking at FIGS. 1 and 2, the sprayer 10 includes a housing 20 having a lower housing section 22 with a circular bottom wall 23 and an outer wall 24 that extends upward from the bottom wall 23. The lower housing section 22 includes upwardly extending hollow battery compartments 25a, 25b for containing batteries as an energy source for the sprayer 10. Any number of batteries of any type may be employed. A removable cover 26 provides access to the battery compartments 25a, 25b so that a user can replace discharged batteries. The cover 26 can be secured to the bottom wall 23 of the lower housing section 22 by a suitable fastener such as a screw, and O-rings 27a, 27b provide a watertight seal between the cover 26 and the bottom wall 23 of the lower housing section 22. The lower housing section 22 can be formed from a polymeric material such as polyethylene or polypropylene.

The sprayer 10 also includes a bottle coupler 30 having an outer wall 31, and a top wall 32, and an open end 33 opposite the top wall 32. The outer wall 31 and the top wall 32 define a generally cylindrical interior space in the bottle coupler 30. The bottle coupler 30 includes a first tubular conduit 35 and a second tubular conduit 36. The first tubular conduit 35 defines a liquid passageway in fluid communication with the interior space in the bottle coupler 30. The second conduit 36 defines an air vent passageway in fluid communication with the interior space in the bottle coupler 30. The bottle coupler 30 is mounted in a hole in the bottom wall 23 of the lower housing section 22. The inner surface of the outer wall 31 of the bottle coupler 30 includes threads that are dimensioned to matingly engage the external threads 18 on the neck 17 of the bottle 16 when the neck 17 of the bottle 16 is screwed into the interior space in the bottle coupler 30. Optionally, the bottle coupler 30 mates with a dip tube that is provided in the bottle 16.

Figure 12:
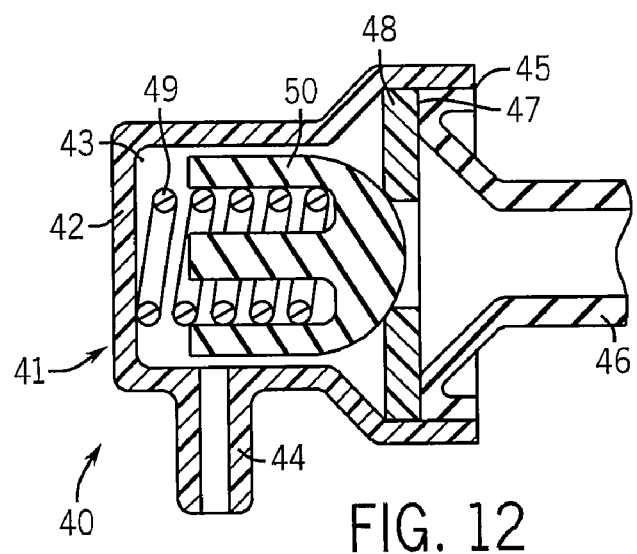
FIG. 12 is a cross-sectional view of an air vent valve suitable for use with an automated sprayer in accordance with the invention.

Referring now to FIGS. 1, 2 and 12, the sprayer 10 also includes a check valve 40 that provides for venting of the bottle 16 from the atmosphere. Air replaces the volume of liquid drawn into the pump of the sprayer, and prevents the bottle 16 from collapsing. The check valve 40 includes a valve housing 41 having an outer wall 42 that defines an interior space 43 of the check valve 40. A first conduit 44 provides an air flow path into the interior space 43. The check valve 40 has an open end 45, and has a second conduit 46 with a generally funnel shaped end that is press fit into the open end 45. An annular valve seat 47 is provided on the funnel shaped end of the second conduit 46. The check valve 40 includes a flexible annular valve seal 48 that seats against the annular valve seat 47 when the check valve 40 is in the normally closed position shown in FIG. 12. The check valve 40 includes a helical compression spring 49 that biases an umbrella shaped valve element 50 against the valve seal 48 to keep the valve seal 48 in the normally closed position. In an example form of the check valve 40, the valve seal 48 can be formed from an elastomeric material, the spring can be formed from carbon or stainless steel, and the remaining components of the check valve 40 can be formed from a polymeric material such as polyethylene or polypropylene.

The first conduit 44 of the check valve 40 can be press fit into the second conduit 36 of the bottle coupler 30 such that the first conduit 44 is placed in fluid communication with the interior space in the bottle coupler 30 and the bottle 16 which is mounted to the bottle coupler 30. Negative pressure can build in the bottle 16 when liquid is withdrawn from the bottle 16. The negative pressure overcomes the biasing force of the spring 49 and/or the sealing force of the annular valve seal 48 against the annular valve seat 47 such that atmospheric air flows between the annular valve seal 48 and the annular valve seat 47, into the interior space 43 of the check valve 40, through the first conduit 44, into the interior space in the bottle coupler 30 and into the bottle 16 to provide venting. Alternatively, any other type of check valve suitable for aspiration of air into the bottle 16 may be used.

Looking at FIGS. 1 and 2, the housing 20 of the sprayer 10 also includes a generally circular middle housing section 56 which can be formed from a polymeric material such as polyethylene or polypropylene. The middle housing section 56 has a mounting bracket 57 for engaging a lower end of the hook 12 (see FIG. 4). An actuator button 59 is assembled in a wall 60 of the middle housing section 56. The middle housing section 56 can be assembled to the lower housing section 22 by a press fit in which a lower rim 61 of the middle housing section 56 engages the lower housing section 22 in an interference fit. An O-ring 65 provides a water tight seal between the middle housing section 56 and the lower housing section 22. Control circuitry 63 is arranged in the middle housing section 56. The functioning of a control circuit of the control circuitry 63 will be described below.

Figure 8:
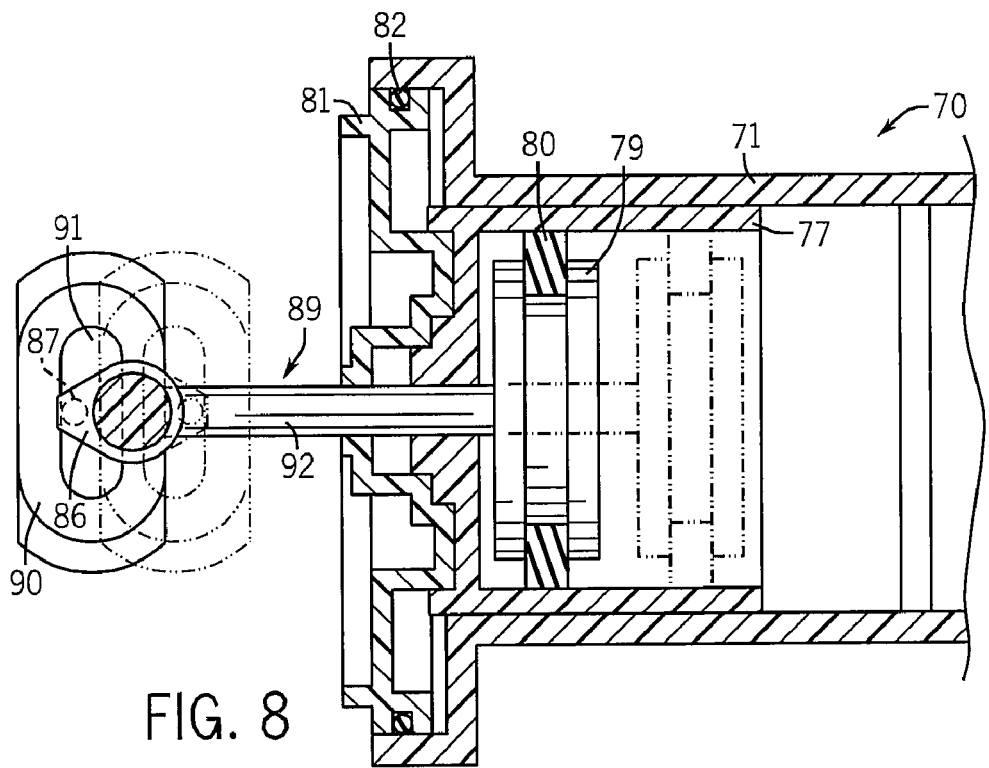
FIG. 8 is a cross-sectional view taken along line 8-8 of FIG. 6.
Figure 9:
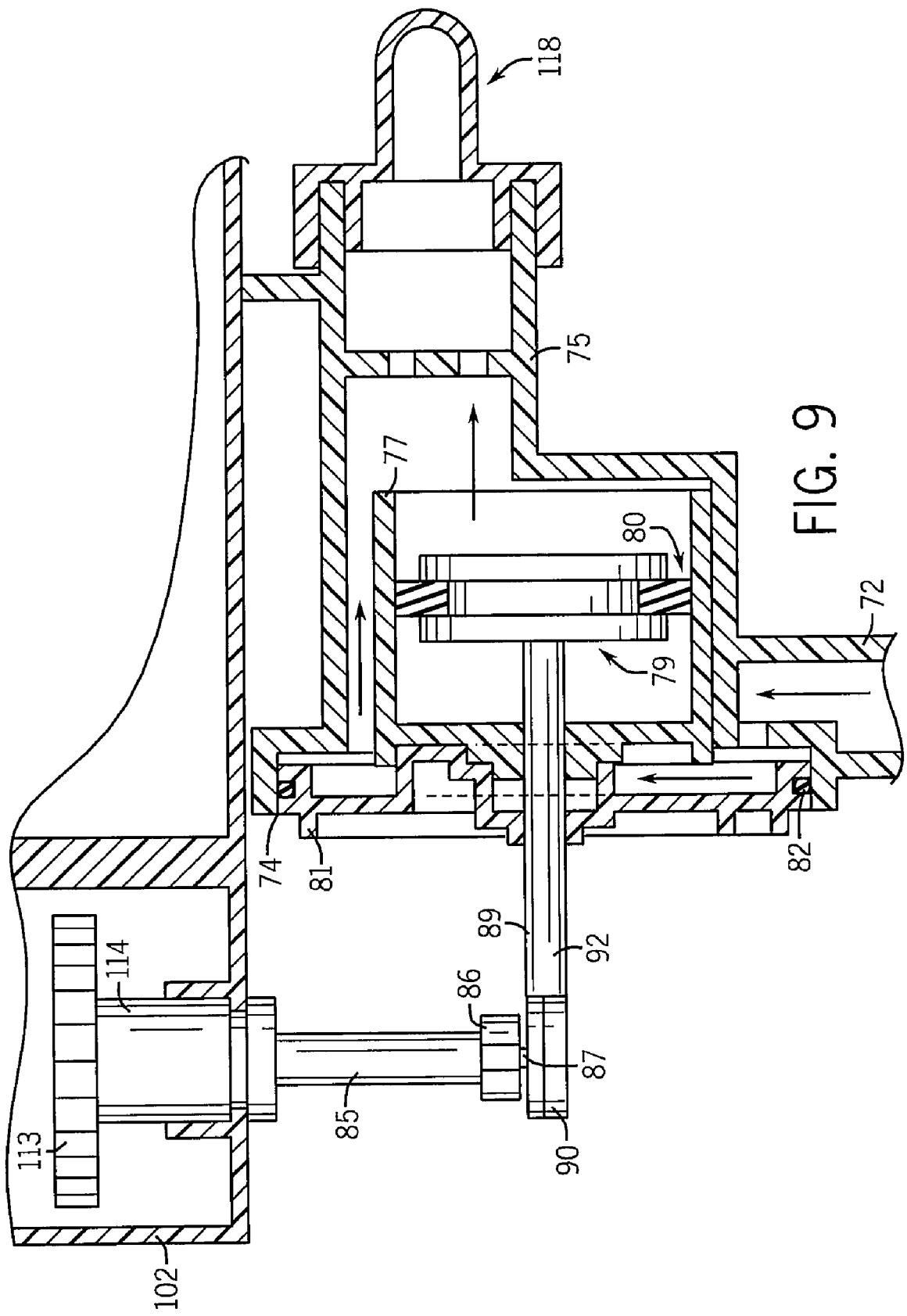
FIG. 9 is a cross-sectional view taken along line 9-9 of FIG. 6.

Referring now to FIGS. 2, 8 and 9, the sprayer 10 also includes a pump 70. While the illustrated pump 70 is a piston pump, other types of pump such as diaphragm pump, a peristaltic pump, or a gear pump can be used in the sprayer 10. The pump 70 includes a pump housing 71 having an inlet conduit 72, an open end 74, and an outlet conduit 75. A one way check valve is provided upstream of the inlet conduit 72. The one way check valve prevents liquid from flowing away from the inlet conduit 72 such that the pump remains primed and liquid does not flow back into the bottle 16. Hollow tubing 53 places the first tubular conduit 35 of the bottle coupler 30 and the inlet conduit 72 of the pump 70 in fluid communication. A pump cylinder 77 is located in the pump housing 71 as shown in FIGS. 8 and 9. A piston 79 reciprocates in the pump cylinder 77, and a piston seal 80 assures a sealing fit against the inner surface of the pump cylinder 77 during operation of the pump 70. A cover 81 closes off the open end 74 of the pump 70 with an O-ring 82 providing a fluid tight seal. The pump 70 includes a pump drive shaft 85 having an eccentric 86 with a downwardly extending pin 87. The pump 70 also includes a push rod 89 having an oblong end 90 with an opening 91 and having a stem 92 that connects the oblong end 90 with the piston 79.

Figure 5:
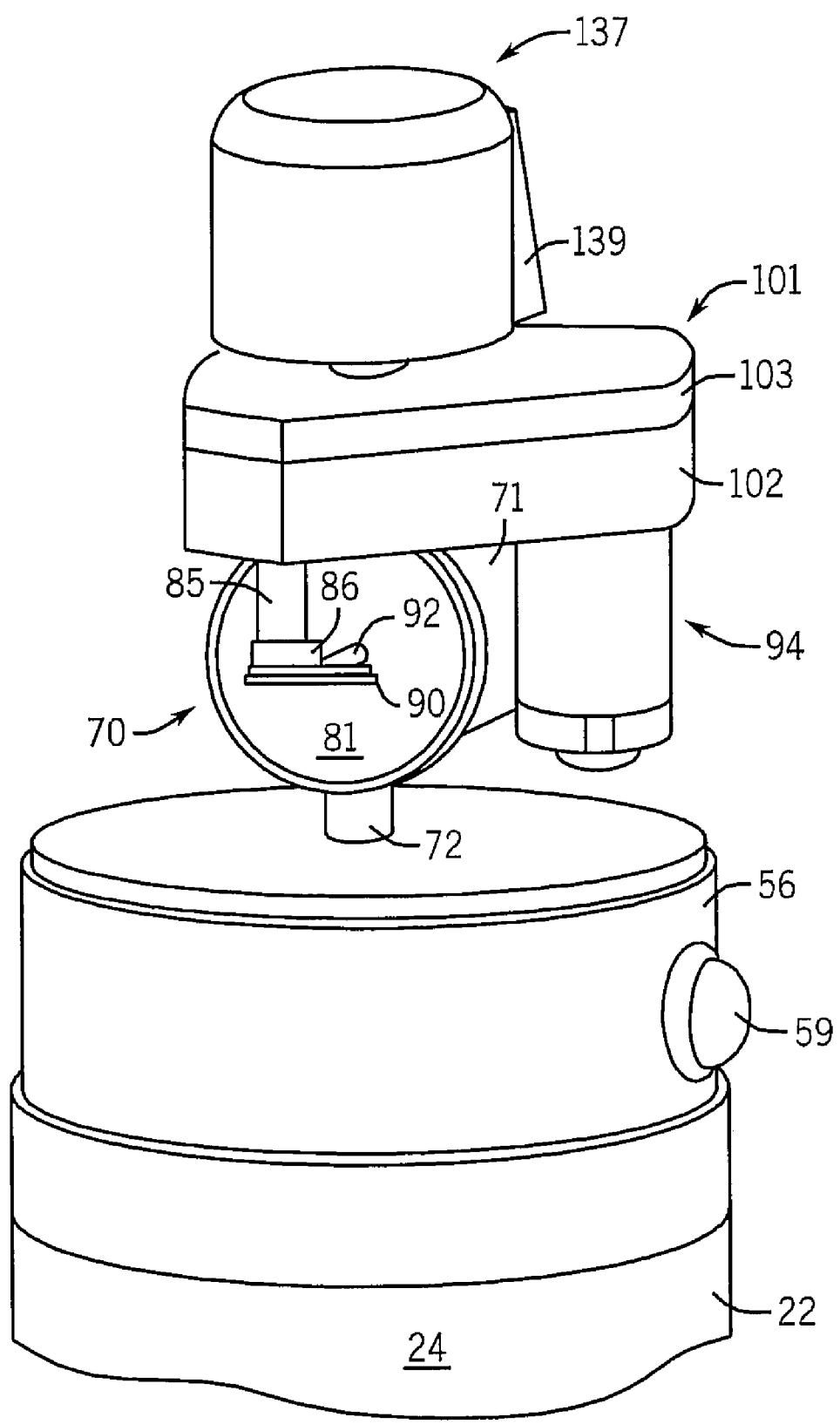
FIG. 5 is a partial perspective view of the sprayer head (with the upper housing removed) of the automated sprayer of FIG. 1.
Figure 6:
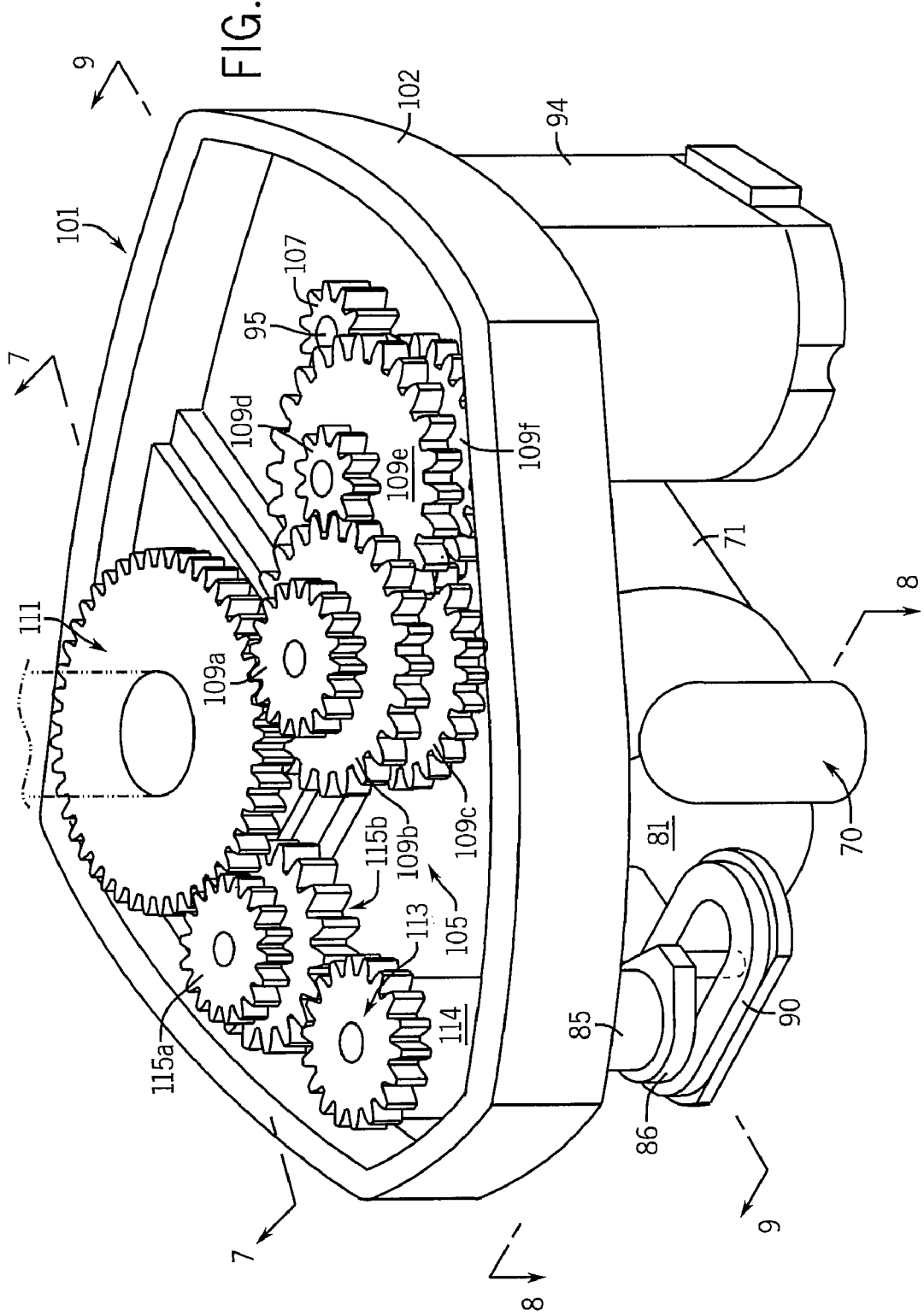
FIG. 6 is a perspective view of the motor, pump, and gear box assembly (with the upper gear case section removed) of the automated sprayer of FIG. 1.

Looking at FIGS. 2, 5 and 6, the pump 70 has a direct current motor 94 having a single drive shaft 95. Suitable wiring (not shown) places the motor 94 in electrical communication with the control circuitry 63. Wiring (not shown) also places the batteries in the battery compartments 25a, 25b in electrical communication with the control circuitry 63. Wiring (not shown) also places the actuator button 59 in electrical communication with the control circuitry 63. The functioning of the control circuitry 63 will be described below.

Referring now to FIGS. 2, 5, 6 and 7, the sprayer 10 also includes a gear box assembly 101 for transmitting mechanical power from the motor 94 to the pump 70. The gear box assembly 101 includes a case having a lower case section 102 and a mating upper case section 103. A gear drive train 105 is housed in the case. Looking at FIG. 6, the gear drive train 105 includes a pinion gear 107 coupled to the drive shaft 95 of the motor 94. Gears 109a, 190b, 190c, 109d, 109e and 109f transmit rotation of the pinion gear 107 to a spray nozzle drive gear 111. The gear drive train 105 also includes a pump drive gear 113 that is coupled to a shaft 114. Gears 115a, 115b transmit rotation from the spray nozzle drive gear 111 to the pump drive gear 113. The gear box assembly 101 also includes a hollow fluid inlet 116 having a projection 117. The fluid inlet 116 is located in an aperture in the lower case section 102 of the gear box assembly 101. Hollow tubing 118 connects the fluid inlet 116 and the outlet conduit 75 of the pump 70 to place the fluid inlet 116 and the pump 70 in fluid communication (see FIGS. 7 and 9).

The gear box assembly 101 may include a different number of gears in meshing relationship, and axles can be operably connected to the gears. The gear box assembly 101 provides a linkage for transferring rotational movement of the drive shaft 95 of the motor 94 to the pump 70 and/or to the rotating dome-shaped spray head 137. While one example of a suitable gear/axle configuration is depicted in FIG. 6, it should be appreciated that any other suitable gears and linkages may be provided to transfer movement of the motor drive shaft 95 to components of the automated sprayer 10.

Looking at FIGS. 1-4 and 7, the sprayer 10 includes an upper housing section 119 which can be formed from a polymeric material such as polyethylene or polypropylene. The upper housing section 119 has a well 122 having an opening 123 in its bottom wall, and a fastener hole 124 in its domed top wall 125. A circular side wall 126 depends downward from the top wall 125 of the upper housing section 119. The middle housing section 56 can be assembled to the upper housing section 119 by a press fit in which an upper rim of the middle housing section 56 engages the upper housing section 119 in an interference fit. An O-ring 127 provides a water tight seal between the middle housing section 56 and the upper housing section 119. A fastener 13 connects the hook 12 to the upper housing section 119 by engaging the wall forming the fastener hole 124.

Referring now to FIGS. 2-4 and 7, the sprayer 10 also includes a rotatable hollow shaft 129 that passes through the opening 123 in the well 122 of the upper housing section 119 and through an aperture in the upper case section 103 of the gear box assembly 101. The shaft 129 is connected to the spray nozzle drive gear 111 by a connecting ring 112. A disk 130 is connected to the shaft 129. The disk 130 is positioned in the well 122 of the upper housing section 119. The sprayer 10 also includes a nozzle 132 for spraying the liquid. The nozzle 132 has a tubular fluid inlet 133 and a spray arm 134. The tubular fluid inlet 133 is in fluid communication with a discharge opening 135 of the spray arm 134. The bottom of the fluid inlet 133 is press fit into the top of the shaft 129. In addition, the sprayer 10 includes a rotating dome-shaped spray head 137 having a side wall 138 with a window 139 forming an aperture 140 in the side wall 138. A top wall 142 extends downwardly from the side wall 138 of the rotating dome-shaped spray head 137. The spray arm 134 of the nozzle 132 is press fit into the aperture 140 in the side wall 138 of the rotating dome-shaped spray head 137.

Figure 10:
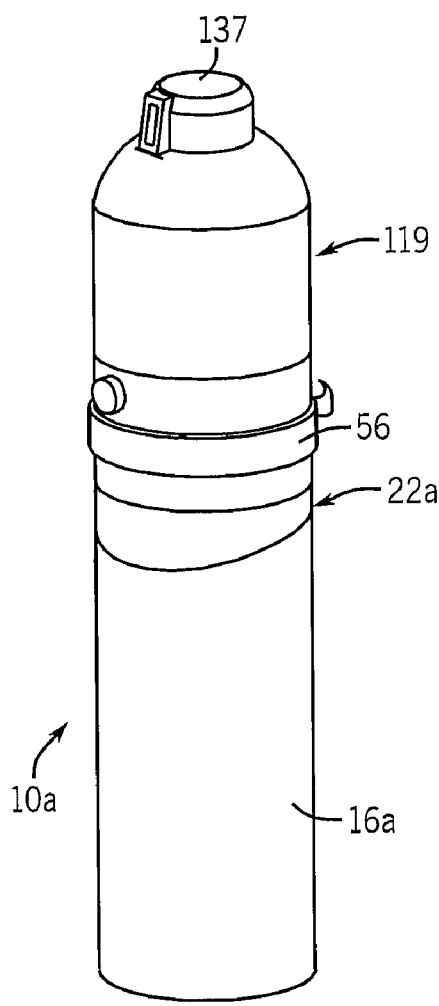
FIG. 10 is a front perspective view of another embodiment of an automated sprayer in accordance with the invention.
Figure 11:
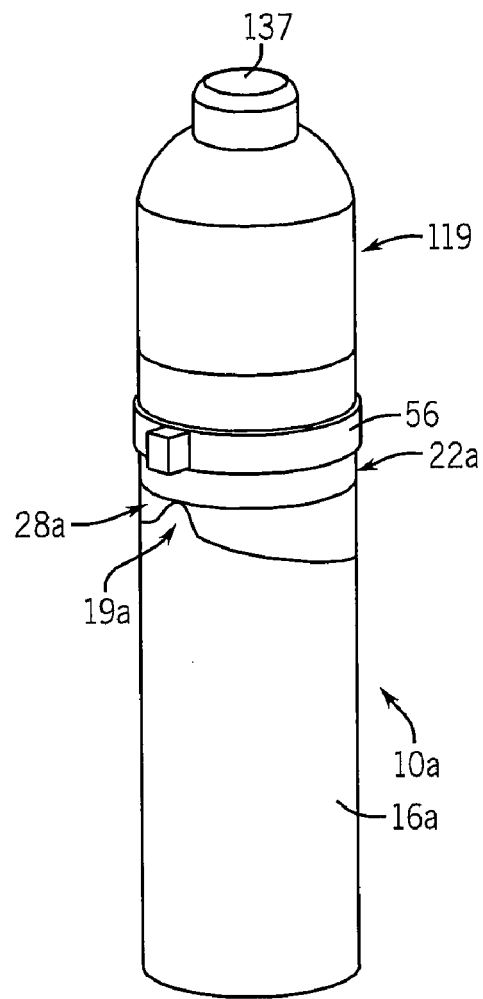
FIG. 11 is a rear perspective view of the automated sprayer of FIG. 10.

Turning now to FIGS. 10 and 11, there is shown another embodiment of an automated sprayer 10*a* in accordance with the invention. The automated sprayer 10*a* includes a middle housing section 56, an upper housing section 119, and a rotating dome-shaped spray head 137 as in the sprayer 10 of FIGS. 1-9. However, the automated sprayer 10*a* includes a bottle 16*a* having an upper ridge having a locater nub 19*a*. The lower housing section 22*a* has a notch 28*a* in the circular bottom wall of the lower housing section 22*a*. In the sprayer 10*a*, the bottle 16*a* is connected to the lower housing section 22*a* by aligning the locater nub 19*a* and the notch 28*a* and moving the bottle 16*a* upward such that the neck of the bottle engages the bottle coupler in a snap fit. The locater nub 19*a* and the notch 28*a* inhibit the use of bottles with improper liquids in that a bottle not having the locater nub 19*a* will not be received and engaged by the lower housing section 22*a*.

Having described the construction of the automated sprayer 10, the liquid flow path through the sprayer 10 can be explained. When the pump 70 is activated, liquid flows upward from the bottle 16 (though any dip tube if provided), through the neck 17, into the interior space of the bottle coupler 30, and through the first tubular conduit 35. Liquid exiting the first tubular conduit 35 flows through hollow tubing 53 past a one way check valve and into the inlet conduit 72 of the pump 70. Looking at FIG. 8, the push rod 89 and attached piston 79 reciprocate from the position shown in full lines to the position shown in broken lines. When the push rod 89 and attached piston 79 move from the position shown in broken lines to the position shown in full lines, the liquid is drawn into the pump cylinder 77 (the upward facing arrows and the top rightward facing arrow in FIG. 9 show this). When the push rod 89 and attached piston 79 move from the position shown in full lines to the position shown in broken lines in FIG. 8, the liquid is expelled from the pump cylinder 77 (the lower rightward facing arrow in FIG. 9 show this). The liquid then enters the hollow tubing 118 after passing through the outlet conduit 75 of the pump 70. After passing through the tubing 118, the liquid enters the hollow fluid inlet 116 by way of projection 117 (see FIGS. 7 and 9). The liquid flows through the fluid inlet 116 and through the hollow shaft 129. The liquid flows through the tubular fluid inlet 133 and then the spray arm 134. The liquid then exits the discharge opening 135 of the spray arm 134 thereby spraying liquid from the sprayer 10.

Having described the components and fluid flow path of the automated sprayer 10, operation of the sprayer 10 can be explained further. When a user wishes to spray an enclosure walls (e.g., shower enclosure walls) with the liquid, he or she simply depresses the button 59 at the front of the sprayer 10. This signals timing circuitry of the control circuitry 63 to begin a countdown delaying spraying for a predetermined time, such as 20 seconds. This affords the user time to exit the shower enclosure and close the doors or curtains. It also may provide the user time to abort the spray cycle by depressing the button 59 a second time. Unless cancelled by the user, the spray cycle begins automatically at the expiration of the countdown. The motor 94 is then energized rotating the drive shaft 95 and attached pinion gear 107 which simultaneously rotates the pump drive gear 113 (by way of the gear drive train 105—see FIG. 6) and turns the spray nozzle drive gear 111 (by way of the gear drive train 105—see FIG. 6).

Looking at FIGS. 8 and 9, as the pump drive gear 113 rotates, shaft 114 rotates thereby rotating the pump drive shaft 85 and the attached eccentric 86 and pin 87. Movement of the pin 87 in the opening 91 in the oblong end 90 of the push rod 89 causes the push rod 89 and attached piston 79 to reciprocate back and forth from the position shown in full lines to the position shown in broken lines in FIG. 8. This provides liquid flow into and out of the pump 70 as described above. Liquid flow from the bottle 16 to the discharge opening 135 of the nozzle 132 proceeds as described above. Thus, the gear box assembly 101 constitutes a transmission that transfers rotational motion of the single motor drive shaft 95 to the pump drive shaft 85 to drive the pump 70.

Figure 7:
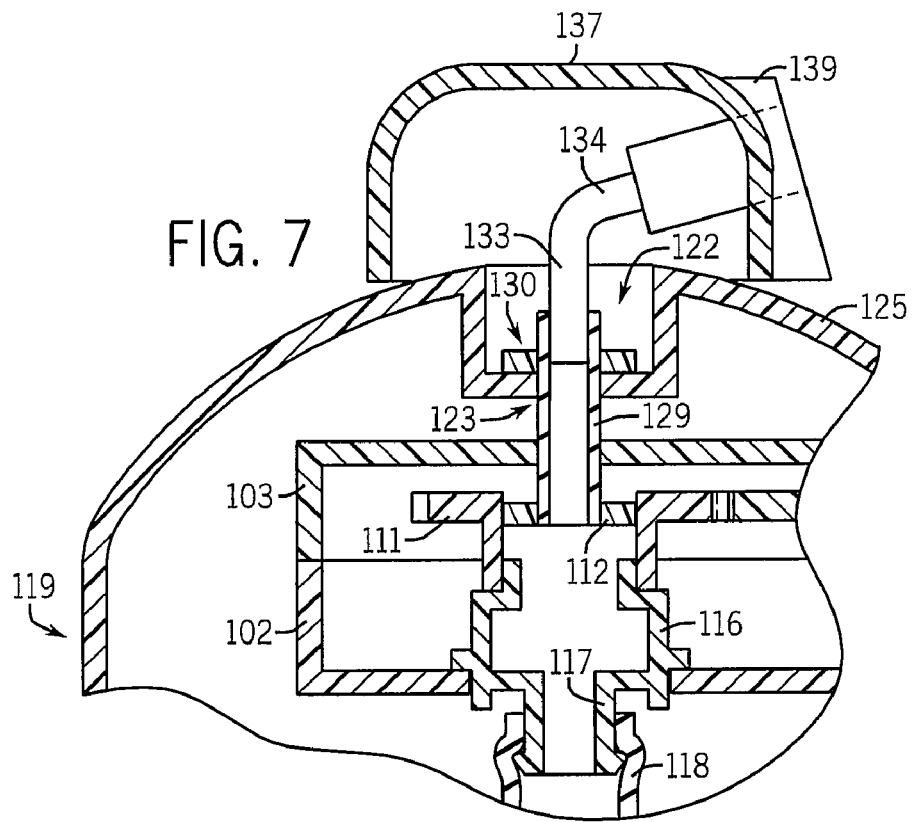
FIG. 7 is a cross-sectional view taken along line 7-7 of FIG. 6.

Looking at FIG. 7, as the spray nozzle drive gear 111 simultaneously rotates with the pump drive gear 113, the shaft 129 (which is connected to the spray nozzle drive gear 111 by the connecting ring 112) rotates. Rotation of the shaft 129, rotates the tubular fluid inlet 133 and attached spray arm 134 of the nozzle 132. Because the spray arm 134 of the nozzle 132 is press fit into the aperture 140 in the side wall 138 of the rotating dome-shaped spray head 137, rotation of the nozzle 132 by the shaft 129 causes the rotating dome-shaped spray head 137 to rotate. Thus, the gear box assembly 101 constitutes a transmission that transfers rotational motion of the single motor drive shaft 95 to rotate the rotatable dome-shaped spray head 137. As a result, rotation of the rotating dome-shaped spray head 137 while the liquid exits the discharge opening 135 of the spray arm 134 causes the liquid to be sprayed radially away from and around the sprayer 10 thereby providing a circular spray pattern. Selection of the discharge opening 135 geometry can control the vertical dimension of the circular spray pattern and the average angle of the spray pattern with respect to the housing 20.

The motor 94 continues to be energized until the expiration of a second countdown performed by the timing circuit, preferably another 20 second interval, automatically initiated by the timer. At that point the motor 94 is deenergized which shuts down the pump 70 and stops rotation of the rotating dome-shaped spray head 137. The sprayer 10 thus returns to a stand-by mode without further intervention from the user, ready for another spray cycle at the demand of the user. In other embodiments, timed release actuation or actuation at a set or selected time may be provided by a suitable programmed or programmable timer or time release device and/or, in some embodiments, actuation may be controlled remotely.

Thus, the invention provides an automated sprayer for spraying the walls of an enclosure with a liquid. It should be noted that the inventive aspects of the invention can be used to dispense a liquid cleaning and/or disinfecting solution to the walls of an enclosure other than a tub/shower surround described herein. For example, an embodiment of the invention designed to mount to the underside of a toilet bowl cover can deliver liquid from a bottle to the toilet bowl. Such a structure should be considered to be an "enclosure" for purposes of this application.

With regard to fastening, mounting, attaching or connecting components of the present invention to form the automated sprayer or components thereof, in accordance with some embodiments of the present invention, unless specifically described otherwise, such are intended to encompass conventional fasteners such as screw threads, threaded connectors, snap rings, detent arrangements, clamps, pins and the like. Components may also be connected by adhesives, glues, welding, ultrasonic welding, and friction fitting or deformation, if appropriate, and appropriate liquid and/or airtight seals or sealing devices may be used. Any electronic portions in accordance with the present invention may use conventional, commercially available electronic components, connectors and devices such as suitable wiring, connectors, printed circuit boards, microchips, sensors, inputs, outputs and the like. Electrical and other components of the invention may be isolated, contained and/or sealed in one or more water and/or fluid-tight chambers, coatings or structures based on environmental or dispensing requirements (e.g., the place of dispensing, the substance to be dispensed, etc.), for example, to prevent or minimize corrosion, leakage, contamination, etc. Unless specifically otherwise disclosed or taught, materials for making the present invention and/or components thereof may be selected from appropriate materials such as metallic materials, ceramic materials, plastic materials and the like, and appropriate manufacturing or production methods including casting, pressing, extruding, molding and machining may be used.

In the foregoing description, embodiments of the present invention, including example embodiments, have been presented for the purpose of illustration and description. They are not intended to be exhaustive or to limit the invention to the precise forms disclosed. Obvious modifications or variations are possible in light of the above teachings. The embodiments were chosen and described to provide the best illustrations of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

INDUSTRIAL APPLICABILITY

The present invention provides a sprayer for automatically spraying the walls of bath and shower enclosures and the like.

What is claimed is:

1. An automated sprayer for spraying an enclosure with a liquid, the sprayer comprising:
a bottle suitable for containing the liquid;
a housing;
a pump in fluid communication with the bottle, the pump being located in the housing;
a rotatable spray head extending axially above an opening in an upper surface of the housing;
a spray nozzle positioned such that an outlet of the spray nozzle is positioned within an opening of the rotatable spray head, the spray nozzle being in fluid communication with an outlet of the pump;
a motor located in the housing; and
a transmission operably coupled to a shaft of the motor, the transmission also being operably coupled to the rotatable spray head, and the transmission also being operably coupled to the pump such that the transmission transfers rotational motion of the shaft to drive the pump and cause rotation of the rotatable spray head.

2. The automated sprayer of claim 1 wherein:
the transmission is a gear box assembly.

3. The automated sprayer of claim 2 wherein:
the pump is operably coupled to a pump drive gear of the gear box assembly.

4. The automated sprayer of claim 2 wherein:
the gear box assembly is enclosed in a case;
the spray nozzle includes a tubular fluid inlet in fluid communication with the outlet of the pump, and
the tubular fluid inlet extends through an aperture in the case.

5. The automated sprayer of claim 4 wherein:
the tubular fluid inlet is mounted in a central opening of a spray nozzle drive gear of the gear box assembly.

6. The automated sprayer of claim 1 further comprising:
a hook for mounting the sprayer,
wherein the housing and the rotatable spray head are located above the bottle when the sprayer is mounted.

7. The automated sprayer of claim 1 wherein:
the housing includes a bottle coupler having internal threads for engaging mating threads on a neck of the bottle.

8. The automated sprayer of claim 7 wherein:
the bottle coupler includes a first conduit defining a liquid passageway in fluid communication with an inlet of the pump and a second conduit defining an air vent passageway in fluid communication with an interior of the housing.

9. The automated sprayer of claim 8 wherein:
the air vent passageway is in fluid communication with a check valve.

10. The automated sprayer of claim 1 further comprising:
a control circuit in electrical communication with a power source and the motor,
wherein the control circuit initiates a spray cycle of the sprayer upon movement of an actuator by providing power from the power source to the motor, and the control circuit automatically terminates the spray cycle by ceasing providing power from the power source to the motor.

11. The automated sprayer of claim 10 wherein:
the control circuit includes a timer that delays providing power from the power source to the motor for a predetermined time after movement of the actuator.

12. The automated sprayer of claim 1 wherein:
a lower end of the housing includes a bottle interface for engaging a neck of the bottle, the bottle interface including at least one compartment for an energy source for the motor.

13. An automated sprayer for spraying an enclosure with a liquid, the sprayer comprising:
a bottle suitable for containing the liquid;
a housing;
a pump in fluid communication with the bottle, the pump being located in the housing;
a rotatable spray head extending axially above an opening in an upper surface of the housing;
a spray nozzle positioned such that an outlet of the spray nozzle is positioned within an opening of the rotatable spray head, the spray nozzle being in fluid communication with an outlet of the pump;
a motor located in the housing;
an energy source in electrical communication with the motor, the energy source being located in the housing;
a gear box assembly located in the housing, a first gear of the gear box assembly being operably coupled to a shaft of the motor, a second gear of the gear box assembly being operably coupled to the rotatable spray head, and a third gear of the gear box assembly being operably coupled to the pump such that the gear box assembly transfers rotational motion of the shaft to drive the pump and to cause rotation of the rotatable spray head; and
a hook for mounting the sprayer,
wherein the housing and the rotatable spray head are located above the bottle when the sprayer is mounted.

14. The automated sprayer of claim 13 wherein:
the gear box assembly is enclosed in a case;
the spray nozzle includes a tubular fluid inlet in fluid communication with the outlet of the pump, and
the tubular fluid inlet extends through an aperture in the case.

15. The automated sprayer of claim 14 wherein:
the tubular fluid inlet is mounted in a central opening of the second gear of the gear box assembly.

16. The automated sprayer of claim 13 further comprising:
a hook for mounting the sprayer,
wherein the gear box assembly is located above the motor and the pump when the sprayer is mounted.

17. The automated sprayer of claim 13 further comprising:
a hook for mounting the sprayer,
wherein the housing and the rotatable spray head are located above the bottle when the sprayer is mounted.

18. An automated sprayer for spraying an enclosure with a liquid, the sprayer comprising:
a bottle suitable for containing the liquid;
a housing;
a pump in fluid communication with the bottle, the pump being located in the housing;
a rotatable spray head extending away from an opening in a surface of the housing;
a spray nozzle positioned such that an outlet of the spray nozzle is positioned within an opening of the rotatable spray head, the spray nozzle being in fluid communication with an outlet of the pump;
a motor located in the housing; and
a transmission operably coupled to a shaft of the motor, the transmission also being operably coupled to the rotatable spray head, and the transmission also being operably coupled to the pump such that the transmission transfers rotational motion of the shaft to drive the pump and cause rotation of the rotatable spray head;
wherein the transmission is a gear box assembly, wherein the pump is operably connected to a pump drive gear of the gear box assembly, and wherein the pump drive gear is operably coupled to a push rod that reciprocates a piston in a cylinder of the pump.

* * * * *